United States Patent [19]

Hoffman et al.

[11] Patent Number: 4,937,264

[45] Date of Patent: Jun. 26, 1990

[54] ANTIHYPERCHOLESTEROLEMIC COMPOUNDS

[75] Inventors: William F. Hoffman; Ta J. Lee, both of Lansdale; Clarence S. Rooney, Worcester, all of Pa.

[73] Assignee: Merck & Co., Inc., Rahway, N.J.

[21] Appl. No.: 377,665

[22] Filed: Jun. 30, 1989

Related U.S. Application Data

[60] Division of Ser. No. 205,406, Jun. 10, 1988, Pat. No. 4,864,038, which is a continuation-in-part of Ser. No. 859,513, May 5, 1986, abandoned.

[51] Int. Cl.[5] .......... A61K 31/365

[52] U.S. Cl. .......... 514/510; 549/292; 514/460; 514/470; 560/9; 560/10; 560/11; 562/431; 562/496

[58] Field of Search .......... 562/431, 496; 549/292; 514/460, 470, 510; 560/9, 10, 11

[56] References Cited

U.S. PATENT DOCUMENTS

| | | | |
|---|---|---|---|
| 3,231,469 | 1/1966 | Canonica | 562/496 |
| 3,546,273 | 12/1970 | Bolhofer | 260/473 |
| 4,153,803 | 5/1979 | Thiele et al. | 562/431 |
| 4,285,951 | 8/1981 | Hoefle | 424/263 |
| 4,444,784 | 4/1984 | Hoffman et al. | 549/292 |
| 4,448,979 | 5/1984 | Terahara et al. | 549/292 |

*Primary Examiner*—Richard L. Raymond
*Assistant Examiner*—Ba K. Trinh
*Attorney, Agent, or Firm*—Melvin Winokur; Joseph F. DiPrima

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) and (II):

(I)

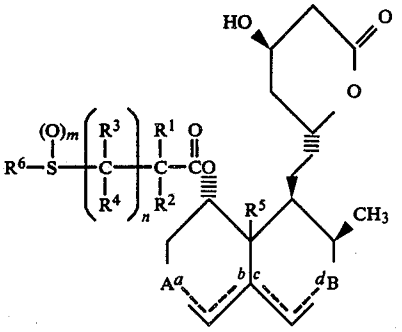

(II)

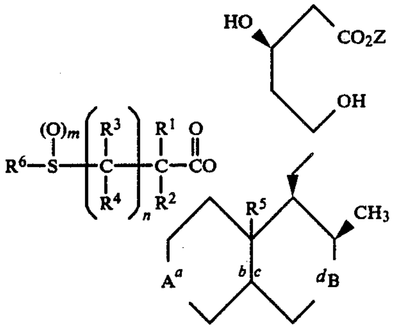

and pharmaceutically acceptable salts of the compounds (II) in which Z is hydrogen are disclosed.

14 Claims, No Drawings

ANTIHYPERCHOLESTEROLEMIC COMPOUNDS

This is a division of application Ser. No. 205,406, filed June 10, 1988, now U.S. Pat. No. 4,864,038; which is a continuation in part of Ser. No. 859,513, filed May 5, 1986, now abandoned.

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occurring compounds and their semi-synthetic analogs have the following general structural formulae:

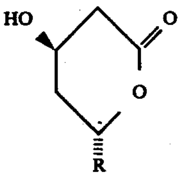
or
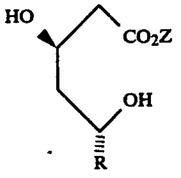

wherein:

Z is hydrogen, $C_{1-5}$ alkyl or $C_{1-5}$ alkyl substituted with a member of the group consisting of phenyl, dimethylamino, or acetylamino;

R is:

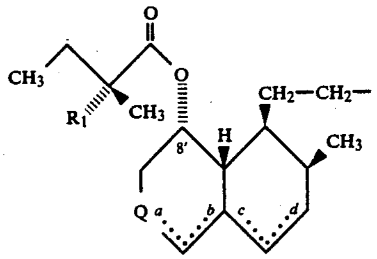

wherein

Q is

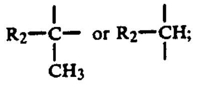

$R_2$ is H or OH:

$R_1$ is hydrogen or methyl; and a, b, c, and d represent optional double bonds, especially where b and d represent double bonds or a, b, c, and d are all single bonds.

U.S. Pat. No. 4,517,373 discloses semisynthetic compounds represented by the above general formula wherein R is

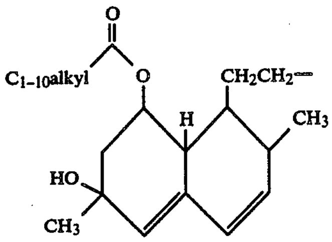
and
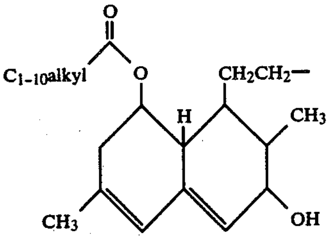

U.S. Pat. No. 4,346,227 and U.S. Pat. No. 4,448,979 also disclose semi-synthetic compounds represented by the above general formula wherein R is

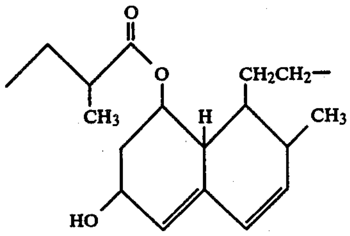
and
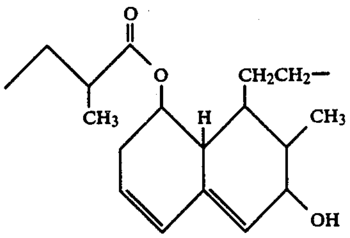

Japanese unexamined patent application No. J59-122,483-A discloses a semi synthetic compound represented by the above general formula wherein R is

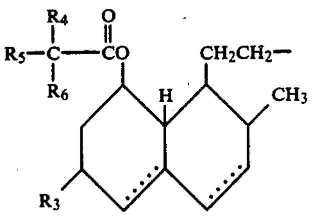

in which $R_3$ is hydrogen or methyl; $R_4$ is hydrogen, halogen or haloalkyl; $R_5$ is hydrogen, halogen or lower alkyl and $R_6$ is halogen, $N_3$, hydroxy, thio, amino, loweralkoxy, lower alkylthio and aralkylthio.

U.S. Pat. No. 4,444,784 discloses 8'-acyloxy derivatives of compactin, mevinolin and the dihydro and tetrahydro analogs thereof. Generically disclosed are the phenyl containing compounds represented by the above general formula wherein R is:

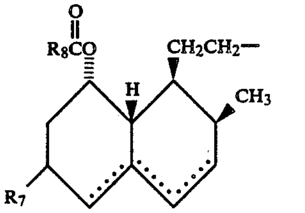

in which $R_7$ is hydrogen or methyl and $R_8$ is $C_{1-10}$ alkyl, $C_{1-10}$ $CF_3$ substituted alkyl, phenyl-$C_{1-3}$alkyl or substituted phenyl-$C_{1-3}$-alkyl in which the substituent is halo, $C_{1-3}$alkyl or $C_{1-3}$alkoxy.

SUMMARY OF THE INVENTION

This invention relates to novel compounds which are HMG-CoA reductase inhibitors and are useful as antihypercholesterolemic agents. Specifically, the compounds of this invention are semi-synthetic analogs of compactin, mevinolin, hydroxylated compactin and hydroxylated mevinolin and the dihydro and tetrahydro analogs thereof which possess a specifically substituted 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

(I)

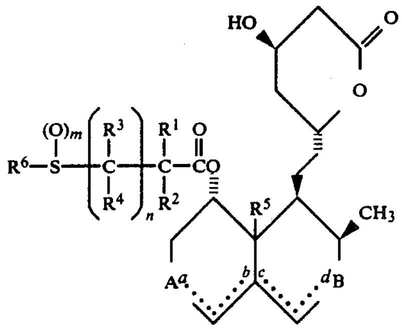

-continued (II)

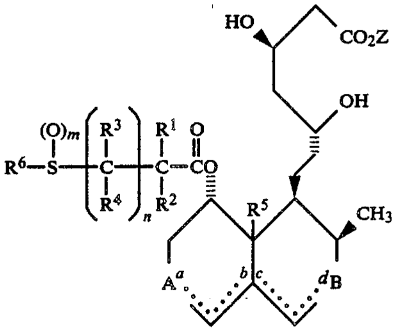

wherein:

m is 0 to 2;

n is 0 to 5;

$R^1$ is $C_{1-3}$alkyl;

$R^2$ is hydrogen or $C_{1-3}$alkyl;

$R^3$ and $R^4$ independently are hydrogen, $C_{1-3}$ alkyl, $C_{3-7}$ cycloalkyl, phenyl or substituted phenyl wherein the substituents are X and Y and when n is 2 to 5, each of the $R^3$s and $R^4$s are independently hydrogen, $C_{1-3}$ alkyl, $C_{3-7}$ cycloalkyl or only one of the $R^3$s and $R^4$s is phenyl or substituted phenyl;

$R^5$ is hydrogen or hydroxy;

$R^6$ is phenyl or substituted phenyl wherein the substitutents are X and Y;

A is

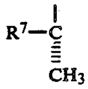 or 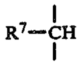

in which $R^7$ is hydrogen or hydroxy;

B $CHR^8$ $R^8$ is which is hydrogen or hydroxy; and a, b, c and d represent single bonds, one of a, b, c or d represents a double bond, or both a and c or both b and d represent double bonds provided that when a is a double bond, A is

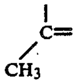 or 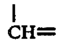

and when d is a double bond, B is

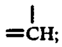;

and

X and Y independently are hydrogen, halogen, trifluoromethyl, $C_{1-3}$ alkyl, nitro, cyano or a group selected from (a) $R^9$ $O(CH_2)_m$ in which m is 0 to 3 and $R^9$ is hydrogen, $C_{1-3}$ alkyl or hydroxy-$C_{1-3}$ alkyl;

(b)

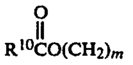 or 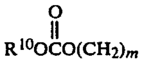

in which $R^{10}$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(-hydroxy-$C_{2-3}$ alkyl)amino-$C_{1-3}$ alkyl;

(c)

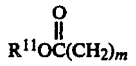

in which $R^{11}$ is hydrogen, $C_{1-3}$ alkyl, hydroxy-$C_{1-3}$ alkyl, $C_{1-3}$ alkoxy-$C_{1-3}$ alkyl, phenyl or naphthyl;

(d) $R^{12}R^{13}N(CH_2)_m$,

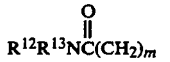
or
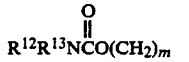

in which and $R^{12}$ $R^{13}$ independently are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl;

(e) $R^{14}S(O)_p(CH_2)_m$ in which p is 0 to 2 and $R^{14}$ is hydrogen, $C_{1-3}$ alkyl, amino, $C_{1-3}$ alkylamino or di ($C_{1-3}$ alkyl) amino;

Z is hydrogen, $C_{1-5}$alkyl or $C_{1-5}$alkyl substituted with a member of the group consisting of phenyl, dimethylamino or acetylamino;

and pharmaceutically acceptable salts of the compounds of the formula (II) in which Z is hydrogen.

Illustrative of one embodiment of this invention are the compounds of the formulae (I) and (II) wherein $R^5$ is hydrogen, $R^7$ is hydrogen, $R^8$ is hydrogen and a, b, c and d represent single bonds or both b and d are double bonds.

Further illustrating this embodiment are those compounds represented by formula (I') wherein n is 0 to 2 and each $R^3$ and $R^4$ is selected from hydrogen or $C_{1-3}$alkyl; and X and Y independently are hydrogen, halogen, hydroxy, amino, trifluoromethyl, $C_{1-3}$alkyl, nitro, cyano, $C_{1-3}$alkoxy, methoxy $C_{1-3}$alkoxy, hydroxymethyl, methylthio or aminomethyl.

(I')

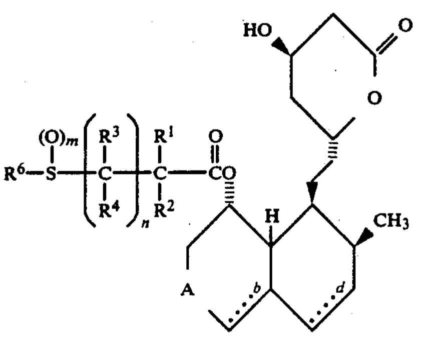

More specifically illustrating this embodiment are those compounds wherein $R^1$ is methyl, $R^2$ is methyl, and $R^3$ and $R^4$ are hydrogen. Exemplifying this embodiment are the following compounds:

(1) 6(R)-[2-[8(S)-[2- methyl-2-(phenylthio)-propionyloxy]-2(S),6(R)-dimethyl-1,2,6,7,8,8a,(R)-hexahydronaphthyl-1(S)]ethyl]-4(R)-hydroxy-3,4,5,6--tetrahydro 2H-pyran-2-one; and (2) 6(R)-[2-[8(S)-[2-methyl-2-(phenylsulfinyl)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

Another embodiment of this invention is the class of compounds of the formula (II) wherein Z is hydrogen or $C_{1-5}$alkyl and pharmaceutically acceptable salts of the compounds of the formula (II) wherein Z is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of formula (I) are conveniently prepared from compactin, mevinolin or the appropriate dihydro or tetrahydro analog thereof via the following general synthetic pathway:

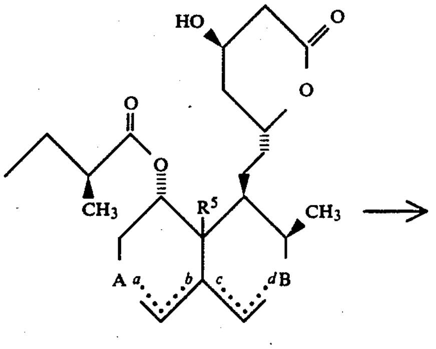

(1)

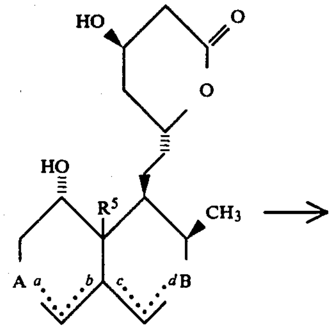

(2)

-continued

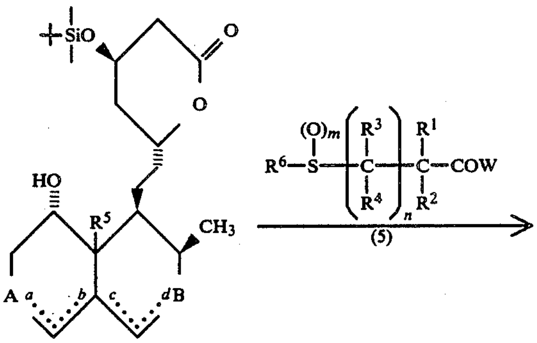

(5)

(3)

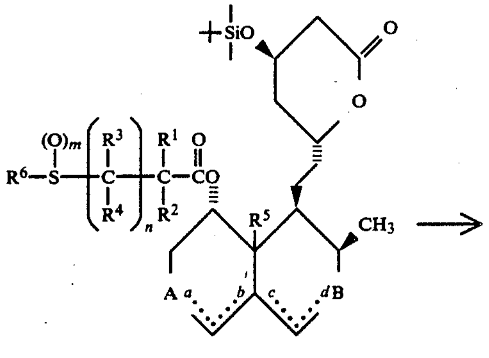

(4)

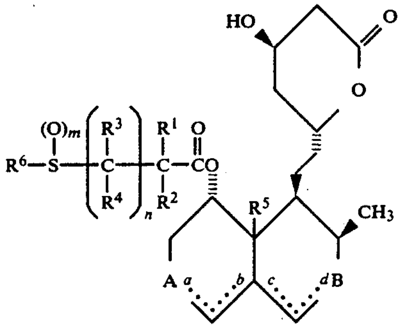

(I)

The starting materials compactin, mevinolin, and their dihydro and tetrahydro analogs are readily available or may be prepared according to fermentation procedures disclosed in U.S. Pat. Nos. 3,983,140, 4,049,495, 4,231,938, 4,294,846, 4,343,814, and the hydrogenation procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784. Acylation of the 8′ hydroxy group of the compounds of the formula (3) is accomplished under suitable conditions utilizing the appropriately substituted acids or acid halides of the formula (5) wherein n, $R^1$, $R^2$, $R^3$, $R^4$ and $R^6$ are as described above, and W is hydroxy, bromo or chloro. The protecting groups of the compound of formula (4) are removed utilizing suitable conditions to afford the compounds of the formula (I). When m is 1 or 2, the acylation of the 8′-hydroxy group is accomplished with the appropriately substituted acid. For the compounds of this invention wherein the polyhydronaphthyl moiety is substituted with a hydroxy group, the compound of the formula (4) is subject to a microbiological hydroxylation after the removal of the protecting groups utilizing the general procedures disclosed in U.S. Pat. Nos. 4,346,227, 4,448,979, 4,517,373 and Japanese Patent Application No. J-60-130,548.

The appropriately substituted acids or acid halides of the formula (5) are commercially available or prepared from known starting materials utilizing standard chemical transformations.

A sequence to such starting materials built on well known literature chemistry and available reactants utilizes the following chemical transformations.

For n=2:

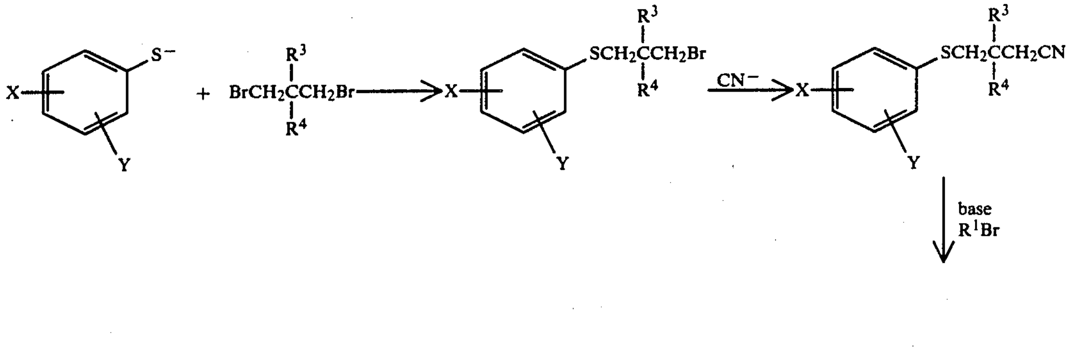

-continued

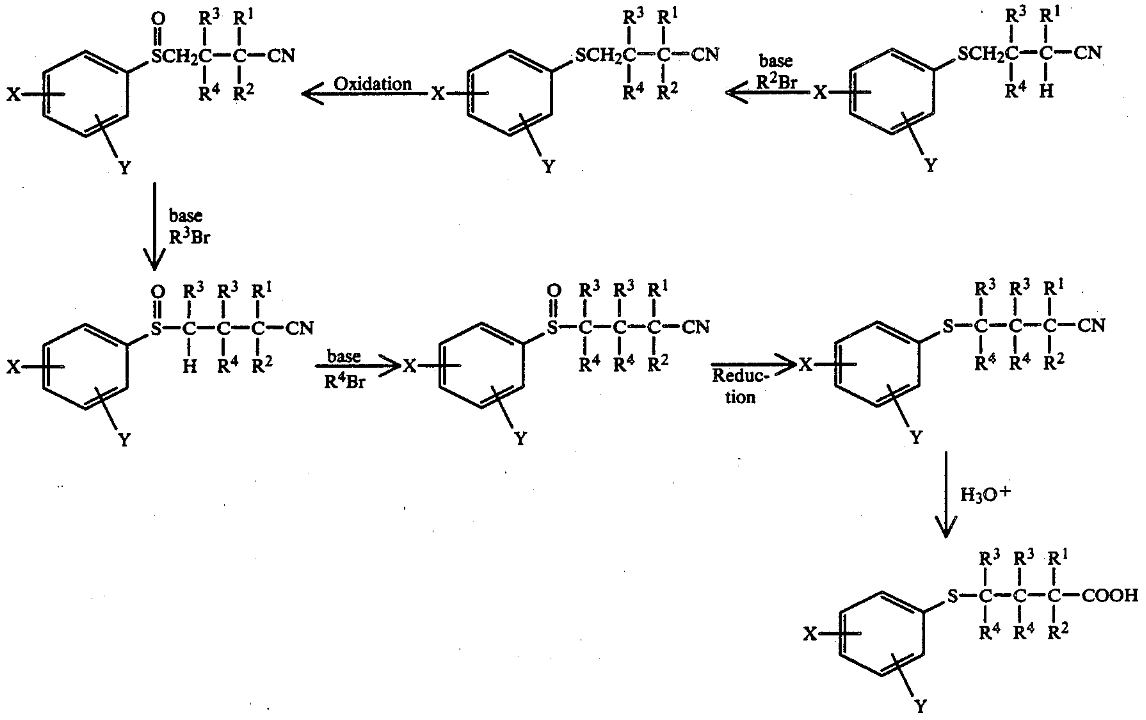

n=1

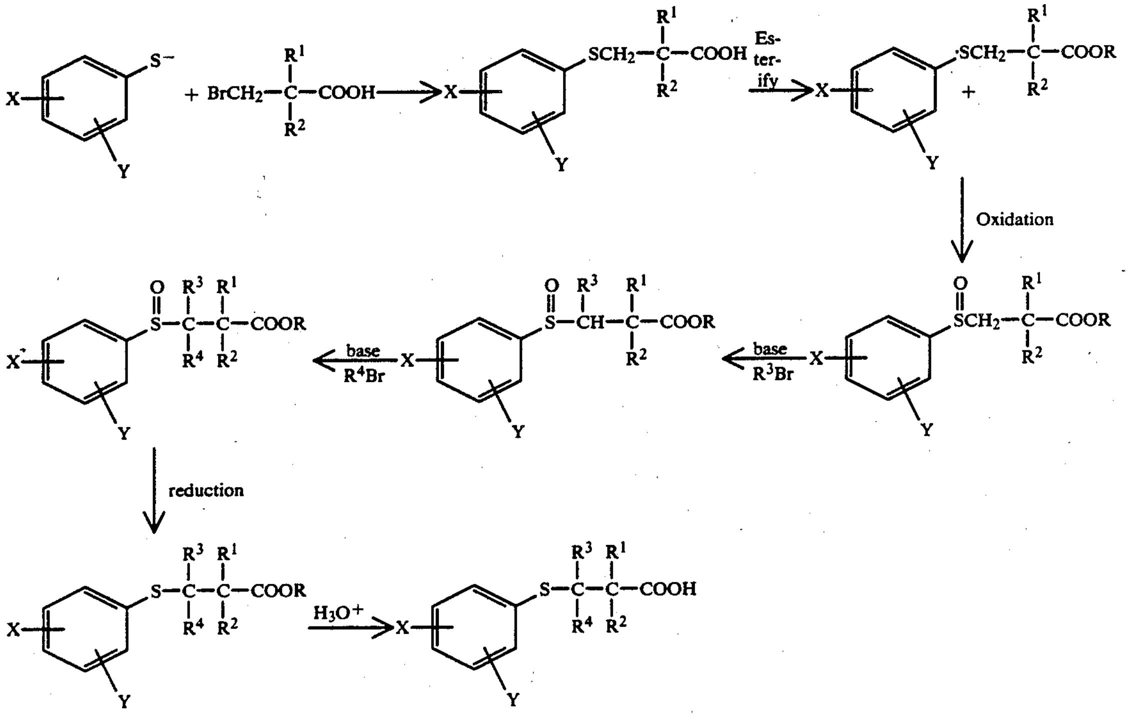

For n=0, one can follow the procedure of Example 1 but substituting a X,Y substituted thiophenol for thiophenol. Alternatively, one could start with an X,Y substituted phenylmercaptan and react it with chloroacetonitrile followed by alkylation at the carbon alpha to the nitrile and hydrolysis to the carboxylic acid following the scheme above (See e.g. M. Makosza, et al. Tetrahedron Letters, 2391 (1972)).

The formation of an arylthioalkyl halide moiety from a arylthio anion and an alkyl dihalide is well known in the art and specifically described in Issari et al., *J. Chem. Soc. Perkin Trans.* II, 1043, (1984). The conversion of an alkyl halide to a nitrile is a standard nucleophilic substitution reaction described in *Organic Reac-*

*tions*, Volume 31, (1984), and Freedman, *J. Org. Chem.*, Vol. 25, 877, (1960). The alpha carbon acidity of nitriles and the alkylation of the nitrile alpha carbon is described in the above mentioned Organic Reactions reference. Conditions and reagents for the oxidation of sulfides to sulfoxides and the reduction of sulfoxides to sulfides are documented in *Comprehensive Organic Chemistry*, Volume 3, 121, Pergaman Press (1979). The formation and alkylation of α-carbanions from sulfoxides is also described in the aforementioned reference. The hydrolysis of nitriles to carboxylic acid is a standard chemical conversion described for example in *Organic Chemistry*, Pine et al., 322, (1980).

The dihalopropane starting materials for the n=2 sequence, such as 1,3-dibromo-2,2-dimethyl-propane described in the Issari reference, are readily available or prepared by standard chemical transformations.

Where n=1, one can begin with a 3-halo-2,2-dialkylpropionic acid and substitute a phenylthiol moiety for the halo leaving group (see e.g. Tanner et al., *Can. J. Chem.* 55, 612 (1977)). The 3-bromopropionic acids can be formed from the 3-hydroxy analog following the method of Greene et al, *J. Am. Chem. Soc.*, 77 3016 (1955). Testa et al, *J. Org. Chem.*, 24 1928 (1959), describe the preparation of a variety of 3-hydroxy-2,2-dialkylpropionic acids.

Alternative to the n=2 sequence described above, one could reduce the carboxylic acid product of the n=1 sequence to an alcohol followed by conversion to the halide and finally reform a nitrile which, as in the n=2 scheme above, can be alkylated at the alpha carbon. Reduction of carboxylic acids to alcohols and transformations of alcohols to alkyl halides are standard reactions described in the Pine organic textbook mentioned above.

The mono- and disubstituted thiophenols which are starting materials in the above schemes are commercially available, or found in the standard chemical literature or can be formed from available thiophenols by classical chemistry. For example, a nitro substituent can be reduced to an amino group which by taking advantage of diazonium salt chemistry can be converted into halide, nitrile, hydroxy, sulfonyl chloride, methyl, carboxy and carbonyl alkyl. (See e.g. J. March, *Advanced Organic Chemistry*, 646, John Wiley & Sons (1985)). It should be noted that a group such as amino may have to be protected during the alkylation sequences described in the above schemes. Such protection can be carried out following the protection descriptions in *Protective Groups in Organic Synthesis*, John Wiley & Sons, (1981).

The oxidation of a sulfide of formula (I) to a sulfoxide can be accomplished employing a mild oxidizing agent such as a peracid (see e.g. Block, Reactions of Organosulfur Compounds, Academic Press (1978)). Further oxidation to sulfones can be conducted using, for example, $H_2O_2$, $KMnO_4$ or $KHSO_5$ (Trost and Curran, *Tetrahedron Letters*, 22, 1287 (1981)).

The compounds of the formula (II) wherein Z is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non reabsorbable form in the gastro-intestinal tract. Examples of such polymers include cholestyramine, colestipol and poly[methyl-(3-trimethylaminopropyl)imino trimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in *J. Med. Chem.*, 28, p. 347–358 (1985) and described below:

Isolation of HMG-CoA Reductase.

Male Holtzman Sprague-Dawley rats (225–250 g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsome by the method of Heller and Shrewsbury [*J. Biol Chem.*, 1976, 251, 3815]and purified through the the second ammonium sulfate precipitation step as described by Kleinsek et al. [*Proc. Natl. Acad. Sci. U.S.A.*, 1977, 74, 1431]. The enzyme preparation was tested for HMG-CoA reductase potency and diluted with 100 mM phosphate buffer (pH 7.2) so that 100 μof the enzyme solution, when added to the assay control, gave a value of 50,000–60,000 dpm. The enzyme preparation was stored at −80° C.

HMG-CoA Reductase Inhibition Assay

The assay is essentially the procedure of Shefer et al. [*J. Lipid Res.*, 1972, 13, 402]. The complete assay medium contained the following in a total volume of 0.8 ml: phosphate buffer, pH 7.2, 100 mM; $MgCl_2$, 3 mM; NADP, 3 mM; glucose 6-phosphate, 10 mM; glucose-6-phosphate dehydrogenase, 3 enzyme units; reduced glutathione, 50 mM; HMG-CoA (glutaryl-3-$^{14}C$, New England Nuclear), 0.2 mM (0.1 μCi); and partially purified enzyme stock solution, 100 μL.

Test compounds or compactin (after first being converted to the sodium salt of their dihydroxy acid form in situ by addition of 1N NaOH (1 equivalent) were added to the assay system in 10-$\mu$L volumes at multiconcentration levels. After a 40-minute incubation at 37° C. with shaking and exposure to air, the reaction was stopped by the addition of 0.4 mL of 8 N HCl. After an additional 30-minute incubation period at 37° C. to ensure the complete lactonization of mevalonic acid to mevalonolactone, 0.2 ml of the mixture was added to an 0.5×5.0 cm column containing 100–200 mesh Bio-Rex 5, chloride form (Bio-Rad), wetted with distilled water, as described by Alberts et al [*J. Proc. Natl. Acad. Sci. U.S.A.*, 1980, 77, 3957]. The unreacted [$^{14}$C]HMG-CoA was absorbed on the resin and the [$^{14}$C]mevalonolactone was eluted with distilled water (2×1 ml) directly into 7-ml scintillation vials. Five milliliters of Aquasol-2 (New England Nuclear) was added to each vial, and radioactivity was measured in a Packard Tri Carb Prias scintillation counter. $IC_{50}$ values were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG-CoA reductase inhibitory activities of the claimed compounds, tabulated below for a number of the claimed compounds are the relative potencies for said compounds.

TABLE 1

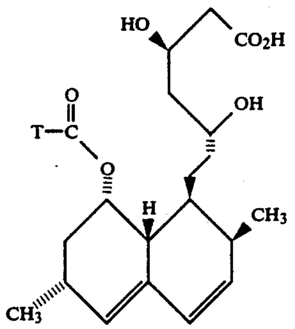

| T | Relative Potency[1] |
|---|---|
| 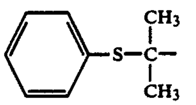 | 156 |
| 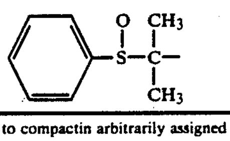 | 38 |

[1]Relative to compactin arbitrarily assigned a value of 100

Included within the scope of this invention is the method of treating arteriosclerosis, familial hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-[2-Methyl-2-(phenylthio)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one

(a) 2-Methyl-2-(phenylthio)-propionic acid (1a)

A stirred mixture of thiophenol (11.0 g, 100 mmol), sodium hydroxide (18.0 g, 450 mmol) and chloroform (14.4 g, 120 mmol) in acetone (100 ml) was gently warmed in a 60° C. water bath. The reaction mixture then exothermed to reflux and was heated at reflux for 3 hours. The acetone was removed in vacuo and the resultant residue dissolved in water (500 ml). The solution was washed with diethyl ether (100 ml) and the aqueous phase was acidified with 12N hydrochloric acid. The resulting mixture was extracted with diethyl ether (3×100 ml). The extracts were combined, washed with brine (2×50 ml) dried over anhydrous magnesium sulfate and concentrated in vacuo to give a yellow liquid. The yellow liquid was distilled at reduced pressure to afford a colorless liquid which solidified on standing bp 0.2 mm=125°-127° C.; mp 62°-64° C.

NMR($CDCl_3$) $\delta$=1.00 (6H, s), 7.31-7.40 (3H, m) 7.52 (2H, m).

(b) 6(R)[2-[(8(S)-[2-Methyl-2-(phenylthio)-propionoyloxy]-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one 1(b)

To a stirred solution of the compound (1a) 0.785 g, 4.0 mmol) and N methylmorpholine (0.44 ml, 4 mmol) in methylene chloride (10 ml) at −5° C. was added dropwise a solution of 2,4-dichloro-6-methoxytriazine (0.72 g, 4.0 mmol) in methylene chloride (10 ml). The reaction mixture was stirred for 1 hour under nitrogen at 0° C. To the reaction mixture was then added dropwise 6(R)-[2[8(S)-hydroxy-2-(S),6(R)-dimethyl-1,2,6,7,8,8a(R)-hexahydronaphthyl-1(S)]-ethyl]4(R)-(tert butyldimethylsilyloxy)-3,4,5,6-tetrahydro-2H-pyran-2-one (870 mg, 2.0 mmol) in methylene chloride (10 ml) and the reaction mixture was heated to reflux. After 24 hours, a solution of the compound (1a) (0.785 g, 4.0 mmol) and 2,4 dichloro-6-methoxytriazine (0.72 g, 4.0 mmol) in methylene chloride (20 ml) was added. After another 48 hours at reflux, the reaction mixture was cooled and poured into diethyl ether (200 ml). The mixture was washed with water (25 ml), 1N hydrochloric acid (10 ml), water (25 ml), saturated aqueous sodium bicarbonate (25 ml) and saturated aqueous sodium chloride (2×25 ml), dried over magnesium sulfate and concentrated in vacuo to give a viscous oil. The oil was chromatographed on a 4×15 cm column of silica gel eluted with 50 percent diethylether/hexane to yield the desired product as a light yellow liquid.

NMR($CDCl_3$) $\delta$=0.01 (6H, s), 0.81 (9H, s), 0.88 (3H, d, J=7 Hz), 1.07 (3H, d, J=7 Hz), 1.37 (3H,s), 1.42 (3H, s), 4.18 (H, m), 4.55 (H, m), 5.34 (H, m), 5.51 (H, m), 5.79 (H, dd, J=6 Hz, 10 Hz), 5.99 (H, d, J=10 Hz), 7.30–7.41 (3H, m), 7.47 (2H, m).

(c)
6(R)-[2-[8(S)-[2-Methyl-2-(phenylthio)-propionoyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (1c)

To a stirred solution of the compound (1b) (640 mg, 1.04 mmol) in tetrahydrofuran (20 ml) were added acetic acid (251 mg, 4.17 mmol) and tetra-n-butylammonium fluoride (3.13 ml, 1M in THF, 3.13 mmol). The reaction mixture was heated to reflux for 4 hours and then cooled. The major portion of the THF was removed in vacuo. The reaction mixture was then poured into diethyl ether (150 ml). The mixture was washed with water (25 ml) 1N hydrochloric acid (10 ml), water (25 ml) saturated sodium bicarbonate (25 ml) and saturated aqueous sodium chloride (2×25 ml), dried over magnesium sulfate and concentrated in vacuo to give a yellow foam. The foam was chromatographed on 3×15 cm column of silica gel eluted with 15 percent isopropanol/hexane, to provide the titled compound which was triturated with hexane to afford the desired product which after recrystallization from diethyl ether/hexane was a colorless solid, m.p. 132°–134° C.

Anal. Calc'd. for $C_{29}H_{38}O_5S$: C, 69.84; H, 7.68.
Found: C, 70.05; H, 8.04.

NMR($CDCl_3$) $\delta$=0.90 (3H, d, J=7 Hz), 1.08 (3H, d, J=7 Hz), 1.39 (3H, s), 1.45 (3H, s) 4.25 (H, m), 4.52 (H, m), 5.41 (H, m), 5.53 (H, m), 5.80 (H, dd, J=6 Hz, 10Hz), 6.00 (H, d, J=10 Hz), 7.30–7.41 (3H, m), 7.49 (2H, m).

EXAMPLE 2

Preparation of
6(R)-[2-[8(S)-[2-Methyl-2-(phenylsulfinyl)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one To a stirred solution of the compound (1c) (99.7 mg, 0.2 mmol) in methylene chloride (10 ml) at −78° C. under nitrogen was added dropwise a solution of 3-chloroperbenzoic acid (34.5 mg, 0.2 mmol) in methylene chloride (5 ml). After one hour, additional 3-chloroperbenzoic acid (34.5 mg, 0.2 mmol) in methylene chloride (5 ml) was added and the reaction mixture stirred for 30 minutes. Dimethylsulfide (100 μl) was then added and the reaction mixture warmed to ambient temperature. The reaction mixture was poured into diethyl ether (200 ml). The solution washed with saturated aqueous sodium bicarbonate (25 ml), and brine (2×25 ml), dried over anhydrous magnesium sulfate and concentrated in vacuo to give a viscous oil. The oil was chromatographed on a 3×12.5 cm column of silica gel eluted with 25 percent isopropanol/hexane to the desired product which after recrystallization from diethyl ether/hexane afforded a colorless solid: mp 117°–119° C.

Anal. Calc'd. for $C_{29}H_{38}O_6S$: C, 67.67; H, 7.44.
Found: C, 68.01; H, 7.75.

NMR($CDCl_3$) $\delta$=0.90 (3H, d, J=7 Hz), 1.10 (3H, d, J=7 Hz), 1.27 (6H, s), 4.30 (H, m), 4.68 (H, m), 5.49 (H, m), 5.53 (H, m), 5.84 (H, m), 6.00 (H, m), 7.49–7.61 (5H, m).

EXAMPLES 3-12

Utilizing the general procedures of Example 1 the following compounds are prepared from the appropriately substituted acid chloride and compactin mevinolin and the dihydro and tetrahydro analogs thereof.

TABLE 2

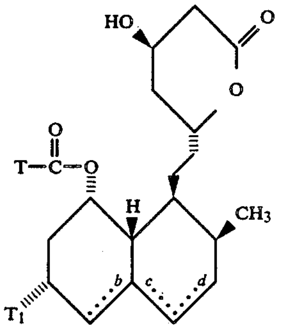

| Compound | T | $T_1$ | b | c | d |
|---|---|---|---|---|---|
| 3 | 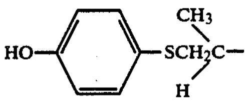 | $CH_3$ | db | — | db |
| 4 | 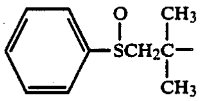 | $CH_3$ | db | — | — |
| 5 | 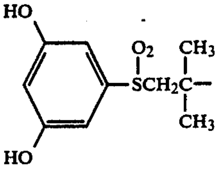 | H | db | — | db |
| 6 | 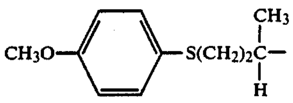 | $CH_3$ | — | — | — |
| 7 | 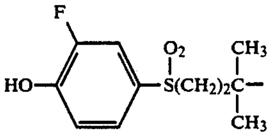 | H | — | db | — |

TABLE 2-continued

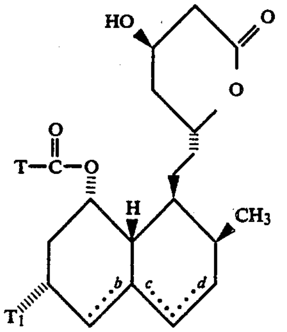

| Compound | T | $T_1$ | b | c | d |
|---|---|---|---|---|---|
| 8 | 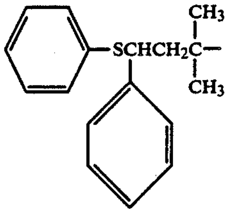 | $CH_3$ | — | — | — |

TABLE 3

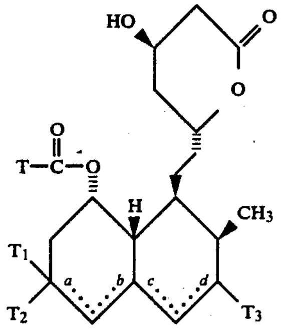

| Compound | T | $T_1$ | $T_2$ | $T_3$ | a | b | c | d |
|---|---|---|---|---|---|---|---|---|
| 9 | 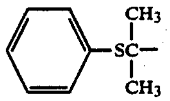 | OH | H | H | — | db | — | db |
| 10 | 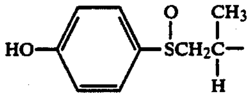 | OH | H | H | — | db | — | db |
| 11 | 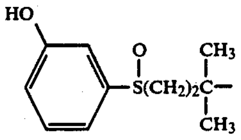 | — | $CH_3$ | OH | db | — | db | — |
| 12 | 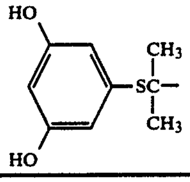 | OH | H | H | — | — | — | — |

db = double bond

EXAMPLE 13

Preparation of Alkali and Alkaline Earth Salts of Compound II

To a solution of the lactone from Example 1(c) (42 mg) in ethanol (2 ml) is added aqueous NaOH (1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 14

Preparation of Methyl Ester of Compound II

To a solution of 400 mg of the lactone from Example 1(e) in 100 ml of absolute methanol is added 10 ml 0.1 M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amyl alcohol, isoamyl alcohol, 2-dimethylamino ethanol, benzyl alcohol, phenethanol, 2-acetamido ethanol, and the like, the corresponding esters are obtained.

EXAMPLE 15

Preparation of free Hydroxy Acids

The sodium salt of the compound II from Example 13 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 16

As a specific embodiment of a composition of this invention, 20 mg of the lactone from Example 1(c) is formulated with sufficient finely divided lactose to provide a total amount of 580 to 590 mg to fill a size 0 hard gelatin capsule.

What is claimed is:

1. A compound represented by the following general structural formula (II'):

(II')

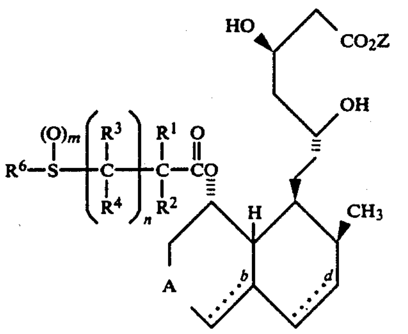

wherein:

m is 0 to 2;

n is 0 to 2;

$R^1$ is $C_{1-3}$ alkyl;

$R^2$ is hydrogen or $C_{1-3}$ alkyl;

each of the $R^3$s and $R^4$s are independently selected from hydrogen or $C_{1-3}$alkyl;

$R^6$ is phenyl or substituted phenyl in which the substituents are X and Y;

A is

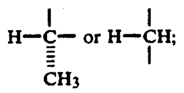

b and d represent single bonds or both b and d represent double bonds; and

X and Y independent are hydrogen, halogen, hydroxy, amino, trifluoromethyl, $C_{1-3}$alkyl, nitro, cyano, $C_{1-3}$alkoxy, methoxy $C_{1-3}$alkoxy, hydroxymethyl, methylthio, or aminomethyl; and Z is hydrogen, $C_{1-5}$alkyl or $C_{1-5}$alkyl substituted with a member of the group consisting of phenyl, dimethylamino, or acetylamino; and pharmaceutically acceptable salts of the compounds of formula (II') in which Z is hydrogen.

2. A compound according to claim 1 wherein n is 0 to 1.

3. A compound according to claim 1 wherein:

$R^1$ is methyl;

$R^2$ is methyl; and $R^3$ and $R^4$ are hydrogen.

4. A compound according to claim 3 which is 7-[1,2,6,7,8,8a(R)-hexahydro-2(S),6(R)-dimethyl-8(S)-[2-methyl-2-(phenylthio)-propionyloxy]-1(S)-naphthyl]-3(R),5(R)-dihydroxyheptanoic acid.

5. A compound according to claim 3 which is 7-[1,2,6,7,8,8a(R)-hexahydro-2(S),6(R)-dimethyl-8(S)-[2-methyl-2-(phenylsulfinyl)-propionyloxy]-1(S)-naphthyl]-3(R), 5(R)-dihydroxyheptanoic acid.

6. A hypocholesterolemic, hypolipidemic pharmaceutical composition comprising a nontoxic therapeutically effective amount of a compound of claim 1 and a pharmaceutically acceptable carrier.

7. A composition according to claim 6 wherein the compound of claim 1 is 0 to 1.

8. A composition according to claim 6 wherein:

$R^1$ is methyl;

$R^2$ is methyl;

$R^3$ and $R^4$ are hydrogen.

9. A composition according to claim 8 in which the therapeutically active ingredient is selected from:

7-[1,2,6,7,8,8a(R)-hexahydro-2(S),6(R)-dimethyl-8(S)-[2-methyl-2-(phenylthio)-propionyloxy]-1(S)-naphthyl]-3(R),5(R)-dihydroxyheptanoic acid;

7-[1,2,6,7,8,8a(R)-hexahydro-2(S),6(R)-dimethyl-8(S)-[2-methyl-2-(phenylsulfinyl)-propionyloxy]-1(S)-napthyl]-3(R),5(R)-dihydroxyheptanoic acid.

10. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

11. A method of inhibiting cholesterol biosynthesis comprising the administration to a subject in need of such treatment a nontoxic therapeutically effective amount of a compound of claim 1.

12. A method according to claim 11 wherein the compound of claim 1 is 0 to 1.

13. A method according to claim 11 wherein:

$R^1$ is methyl;

$R^2$ is methyl;

$R^3$ and $R^4$ are hydrogen.

14. A method according to claim 13 which the therapeutically active ingredient is selected from:

7-[1,2,6,7,8,8a(R)-hexahydro-2(S),6(R)-dimethyl-8(S)-[2-methyl-2-(phenylthio)-propionyloxy]-1(S)-naphthyl]-3(R),5(R)-dihydroxyheptanoic acid;

7-[1,2,6,7,8,8a(R)-hexahydro-2(S),6(R)-dimethyl-8(S)-[2-methyl-2-(phenylsulfinyl)-propionyloxy]-1(S)-naphthyl]-3(R),5(R)-dihydroxyheptanoic acid.

* * * * *